(12) United States Patent
Griego et al.

(10) Patent No.: US 7,052,489 B2
(45) Date of Patent: May 30, 2006

(54) MEDICAL DEVICE WITH DEFLECTING SHAFT AND RELATED METHODS OF MANUFACTURE AND USE

(75) Inventors: John A. Griego, Blackstone, MA (US); Matthew Whitney, Upton, MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 68 days.

(21) Appl. No.: 10/727,626

(22) Filed: Dec. 5, 2003

(65) Prior Publication Data

US 2005/0124912 A1      Jun. 9, 2005

(51) Int. Cl.
*A61B 17/00* (2006.01)
(52) U.S. Cl. .......................... 606/1; 600/139; 600/144
(58) Field of Classification Search .................... 606/1; 600/139, 144
See application file for complete search history.

(56) References Cited

U.S. PATENT DOCUMENTS

| | | | |
|---|---|---|---|
| 4,982,727 A | 1/1991 | Sato | |
| 5,632,764 A | 5/1997 | Beideman et al. | |
| 5,666,965 A | 9/1997 | Bales et al. | |
| 5,741,429 A * | 4/1998 | Donadio et al. | ................ 216/8 |
| 5,967,997 A | 10/1999 | Turturro et al. | |
| 5,971,940 A | 10/1999 | Baker et al. | |
| 6,569,105 B1 * | 5/2003 | Kortenbach et al. | ........ 600/562 |
| 2001/0047124 A1 | 11/2001 | Yamamoto | |
| 2002/0017515 A1 | 2/2002 | Obata et al. | |

FOREIGN PATENT DOCUMENTS

WO        WO 97/12557 A        4/1997

* cited by examiner

*Primary Examiner*—Beverly M. Flanagan
*Assistant Examiner*—Matthew J. Kasztejna
(74) *Attorney, Agent, or Firm*—Finnegan Henderson Farabow Garrett & Dunner, L.L.P.

(57) ABSTRACT

Various embodiments of a medical device having a deflecting shaft and related methods of manufacture and use are disclosed. For example, the device may include a proximal handle, a distal assembly for performing a medical procedure, and a wire coil connecting the proximal handle to the distal assembly, wherein actuation of the proximal handle may cause the distal assembly to perform the medical procedure. The wire coil may have a proximal portion comprised of a first wire and a distal portion comprised of a second wire. The second wire may have a diameter less than a diameter of the first wire so that the distal portion of the wire coil may have a flexibility greater than a flexibility of the proximal portion.

64 Claims, 7 Drawing Sheets

MEDICAL DEVICE WITH DEFLECTING SHAFT AND RELATED METHODS OF MANUFACTURE AND USE

DESCRIPTION OF THE INVENTION

1. Field of the Invention

Embodiments of the invention relate to medical devices having deflecting shafts and related methods thereof. In a particular embodiment, the invention relates to a shaft having a deflectable distal portion for use with an end effector assembly that performs a medical procedure.

2. Description of the Related Art

A number of different types of medical devices are being used to access tissue sites within a patient's body. For example, in a surgical procedure involving severing of tissue within a patient's body, a suitable tissue cutting device, such as, for example, biopsy forceps, a snare, or scissors, may be used, typically in conjunction with endoscopic assistance. Such a tissue acquisition device may include an elongated, tubular control shaft, made of, for example, a wire coil, through which one or more actuation wires pass. This shaft generally requires sufficient flexibility to allow advancement of the device through a tortuous body cavity, but it also requires sufficient stiffness to prevent lumen collapse when tension on the actuation wires is generated.

During a surgical procedure, for example, a physician may require access to tissue that is not aligned axially with the axis of an end effector assembly connected to a control shaft. The physician then must manipulate the control shaft and/or the end effector assembly to access the tissue. This manipulation is difficult due to the stiffness of the control shaft, which may limit deflective movement of the control shaft and the end effector assembly connected thereto. Consequently, the physician may not be able to access certain tissues with a given surgical device. While the physician may alternatively manipulate the endoscope in which the surgical device is inserted, the manipulation of the endoscope may also be limited due to space limitations inside the body cavity and/or the stiffness of the endoscope itself.

SUMMARY OF THE INVENTION

Therefore, an embodiment of the invention relates to a medical device that enables deflective movement of a control shaft, for example, in its distal portion, thereby permitting access to various tissues that are not aligned axially with respect to the axis of a surgical device. Such an embodiment includes a medical device having a structural mechanism for deflecting the distal portion of a control shaft.

To attain the advantages and in accordance with the purpose of the invention, as embodied and broadly described herein, one aspect of the invention may provide a medical device comprising a proximal handle, a distal assembly for performing a medical procedure, and a wire coil connecting the proximal handle to the distal assembly, where the actuation of the proximal handle may cause the distal assembly to perform the medical procedure. The wire coil may have a proximal portion comprised of a first wire and a distal portion comprised of a second wire, wherein the second wire may have a diameter less than a diameter of the first wire, so that the distal portion of the wire coil may have a flexibility greater than a flexibility of the proximal portion.

In an aspect, the wire coil at the distal portion may have an outer diameter that is less than an outer diameter of the wire coil at the proximal portion. The device may be configured to selectively deflect the distal portion relative to the proximal portion.

Another aspect of the invention may include a jacket covering an outer surface of the proximal portion. In still another aspect, the proximal portion may include a first outer jacket and the distal portion may include a second outer jacket, wherein the second outer jacket may be made of a material different than a material of the first outer jacket. The second outer jacket material may be softer than the first outer jacket material.

In yet still another aspect of the invention, actuation of the handle may cause at least one of actuation of the distal assembly and deflection of the distal portion. For example, actuation of the handle from a first position to a second position may actuate the distal assembly, and actuation of the handle from the second position to a third position may deflect the distal portion relative to the proximal portion. The handle may include a stationary part and a movable part movable relative to the stationary part between the first, second, and third positions. In addition, the movable part may be axially reciprocally movable relative to the stationary part.

In another aspect of the invention, the device may include a deflection control member configured to hold the distal portion in a deflected position. The handle may include a first actuation member for actuating the distal assembly and a second actuation member for deflecting the distal portion.

In still another aspect of the invention, the device may include a deflection control member for controlling the deflection of the distal portion relative to the proximal portion.

In yet still another aspect of the invention, the distal assembly may include a biopsy forceps assembly.

According to another aspect of the invention, a medical device may comprise a proximal handle, a distal assembly for performing a medical procedure, and an elongated member connecting the proximal handle to the distal assembly. The elongated member may have a proximal portion and a distal portion, where the distal portion may have a flexibility greater than a flexibility of the proximal portion so as to selectively deflect the distal portion relative to the proximal portion. In an aspect, actuation of a moving part of the proximal handle may cause both deflection of the distal portion and actuation of the distal assembly to perform the medical procedure.

In another aspect of the invention, the elongated member may include a wire coil. The wire coil at the distal portion may have an outer diameter that is less than an outer diameter of the wire coil at the proximal portion. The distal portion may be made of a first wire and the proximal portion may be made of a second wire, where the first wire may have a diameter less than a diameter of the second wire.

In still another aspect of the invention, the device may include a jacket covering an outer surface of the proximal portion of the elongated member. In another aspect, the proximal portion may include a first outer jacket and the distal portion may include a second outer jacket, where the second outer jacket may be made of a material different than a material of the first outer jacket, so that the distal portion may be more flexible than the proximal portion. The second outer jacket material may be softer than the first outer jacket material. The elongated member may include a wire coil made of a wire having substantially the same diameter.

In yet still another aspect of the invention, the movable part may be configured to actuate from a first position to a second position to actuate the distal assembly and from the second position to a third position to deflect the distal portion relative to the proximal portion. The movable part may move relative to a stationary part of the handle between the first, second, and third positions. The movable part may also be axially reciprocally movable relative to the stationary part.

Another aspect of the invention may provide a deflection control member configured to hold the distal portion in a deflected position. Alternatively, in still another aspect of the invention, the device may provided with a deflection control member for controlling the deflection of the distal portion relative to the proximal portion.

According to still another aspect of the present invention, a medical device may comprise a proximal handle, a distal assembly for performing a medical procedure, and an elongated member connecting the proximal handle to the distal assembly, where actuation of the proximal handle may cause the distal assembly to perform the medical procedure. The elongated member may have a distal portion and a proximal portion. The device may also includes a first outer jacket covering at least a portion of the proximal portion of the elongated member, and a second outer jacket covering at least a portion of the distal portion of the elongated member. In an aspect, the second outer jacket may be made of a material different than a material of the first outer jacket, so that the distal portion of the elongated member has a flexibility greater than a flexibility of the proximal portion of the elongated member. The second outer jacket material may be softer than the first outer jacket material.

In accordance with another aspect of the invention, an elongated control shaft for use in a medical device may be provided. The shaft may include a wire coil having a proximal portion comprised of a first wire and a distal portion comprised of a second wire, where the wire coil may be configured to connect a handle to a distal assembly. The second wire may have a diameter less than a diameter of the first wire, so that the distal portion of the wire coil may have a flexibility greater than a flexibility of the proximal portion.

In still another aspect of the invention, the wire coil may be configured to selectively deflect the distal portion relative to the proximal portion. For example, the wire coil may include a jacket covering at least a portion of an outer surface of the wire coil. The shaft may also include a deflection control member configured to hold the distal portion in a deflected position. In alternative or in addition, the device may include a deflection control member for controlling the deflection of the distal portion relative to the proximal portion.

Another aspect of the invention may provide an elongated control shaft having an elongated member for connecting a proximal handle to a distal assembly, wherein actuation of the proximal handle may cause the distal assembly to perform a medical procedure. The elongated member may have a proximal portion and a distal portion, a first outer jacket covering at least a portion of the proximal portion of the elongated member, and a second outer jacket covering at least a portion of the distal portion of the elongated member. The second outer jacket may be made of a material different than a material of the first outer jacket, so that the distal portion of the elongated member may have a flexibility greater than a flexibility of the proximal portion of the elongated member. In an aspect, the second outer jacket material may be softer than the first outer jacket material.

In another aspect, the elongated member may includes a wire coil. The distal portion may be made of a first wire and the proximal portion may be made of a second wire, where the first wire may have a diameter less than a diameter of the second wire. Alternatively, the elongated member may include a wire coil made of a wire having substantially the same diameter.

According to still another aspect of invention, a method of making a medical device is provided. The method includes forming an elongated wire coil having a distal portion made of a first wire and a proximal portion made of a second wire, where the first wire may have a diameter less than a diameter of the second wire. The method may also include attaching a proximal handle to the proximal portion, and attaching a distal assembly for performing a medical procedure to the distal portion. The method may also include providing a deflection controller for controlling deflection of the distal portion.

In another aspect of the invention, the method may include jacketing at least a portion of the elongated member. Jacketing may include jacketing the proximal portion of the elongated member and not jacketing the distal portion of the elongated member. Alternatively or in addition, jacketing may include jacketing the distal portion with a first jacket and the proximal portion with a second jacket, wherein the first jacket may be made of a material softer than a material for the second jacket. In an aspect of the invention, the first wire and the second wire may be formed from the same wire. In another aspect of the invention, the first wire may be attached to the second wire. The first wire may be attached to the second wire via a laser welding.

Still another aspect of the invention may include attaching a control member extending from the proximal handle to the distal member, wherein the control member may be configured to control at least one of actuation of the distal assembly and deflection of the distal portion of the elongated member.

In accordance with another aspect of the invention, a method of making a medical device may include providing an elongated member having a distal portion and a proximal portion, jacketing at least a portion of the proximal portion with a first outer jacket, jacketing at least a portion of the distal portion with a second outer jacket, attaching a proximal handle to the proximal portion, and attaching a distal assembly for performing a medical procedure to the distal portion. A material for the second outer jacket may be different from a material for the first outer jacket, so that the distal portion of the elongated member may have a flexibility greater than a flexibility of the proximal portion of the elongated member. The second outer jacket may be made of a material softer than a material for the first jacket.

Another aspect of the invention may include forming the elongated member with a wire coil. Forming the elongated member may include forming the distal portion with a first wire and the proximal portion with a second wire, where the first wire may have a diameter less than a diameter of the second wire. In still another aspect of the invention, the first wire and the second wire may be formed from the same wire. Alternatively, the first wire may be attached to the second wire.

In still another aspect of the invention, a method of performing a medical procedure may be provided. The method may include providing a medical device adjacent to a tissue site, where the medical device may include a proximal handle, a distal assembly, and an elongated wire coil connecting the distal assembly to the proximal handle. The wire coil may include the proximal portion made of a first wire and a distal portion made of a second wire, where the second wire may have a diameter less than a diameter of the first wire, so that the distal portion of the wire coil may have a flexibility greater than a flexibility of the proximal portion. The method may also include deflecting a distal portion of the wire coil to access tissue at the tissue site, and performing the medical procedure on the tissue with the distal assembly. The wire coil may be configured to selectively deflect the distal portion relative to the proximal portion. The wire coil at the distal portion may have an outer diameter that is less than an outer diameter of the wire coil at the proximal portion.

In yet still another aspect of the invention, the handle may include a first actuation member for actuating the distal assembly and a second actuation member for deflecting the distal portion. The wire coil may include a first outer jacket covering an outer surface of the proximal portion of the wire coil. The wire coil may further include a second outer jacket covering an outer surface of the distal portion, where the second outer jacket may be made of a material different than a material of the first outer jacket, so that the distal portion may be more flexible than the proximal portion. The second outer jacket material may be softer than the first outer jacket material.

In another aspect of the invention, actuating the proximal handle may include actuating a movable part of the handle from a first position to a second position to actuate the distal assembly, and actuating the movable part of the handle from the second position to a third position to deflect the distal portion relative to the proximal portion. The movable part of the handle may move relative to a stationary part of the handle between the first, second, and third positions. The method may include holding the distal portion in a deflected position. Holding the distal portion in the deflected position may be performed after deflecting the distal portion and while performing the medical procedure on the tissue. Holding the distal portion in the deflected position may be performed by a deflection control member.

In still another aspect of the invention, the distal assembly may include a biopsy forceps assembly. The method may then include opening the biopsy forceps assembly, receiving the tissue in the biopsy forceps assembly by deflecting the distal portion of the wire coil, and severing the tissue by closing the biopsy forceps assembly. Actuating the proximal handle may include actuating the biopsy forceps assembly to open and close. Alternatively or in addition, actuating the proximal handle may include deflecting the distal portion relative to the proximal portion.

Another aspect of the invention may provide a method of performing a medical procedure comprising providing a medical device adjacent to a tissue site, the medical device including a proximal handle, a distal assembly, and an elongated member connecting the distal assembly to the proximal handle, actuating the distal assembly by actuating a movable part of the handle from a first position to a second position, deflecting the distal portion relative to the proximal portion to access tissue at the tissue site by actuating the movable part of the handle from the second position to a third position, and performing the medical procedure on the tissue with the distal assembly. In still another aspect of the invention, the movable part of the handle may move relative to a stationary part of the handle between the first, second, and third positions. The movable part may be axially reciprocally movable relative to the stationary part.

In still another aspect of the invention, holding the distal portion in the deflected position may be performed after deflecting the distal portion and while performing the medical procedure on the tissue. Holding the distal portion in the deflected position may be performed by a deflection control member.

In yet still another aspect of the invention, actuating the distal assembly may include opening an end effector assembly of the distal assembly, and performing the medical procedure on the tissue may include closing an end effector assembly of the distal assembly.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

In the drawings.

DESCRIPTION OF THE EMBODIMENTS

Reference will now be made in detail to the exemplary embodiments of the invention, examples of which are illustrated in the accompanying drawings. Wherever possible, the same reference numbers will be used throughout the drawings to refer to the same or like parts.

Figure 1:
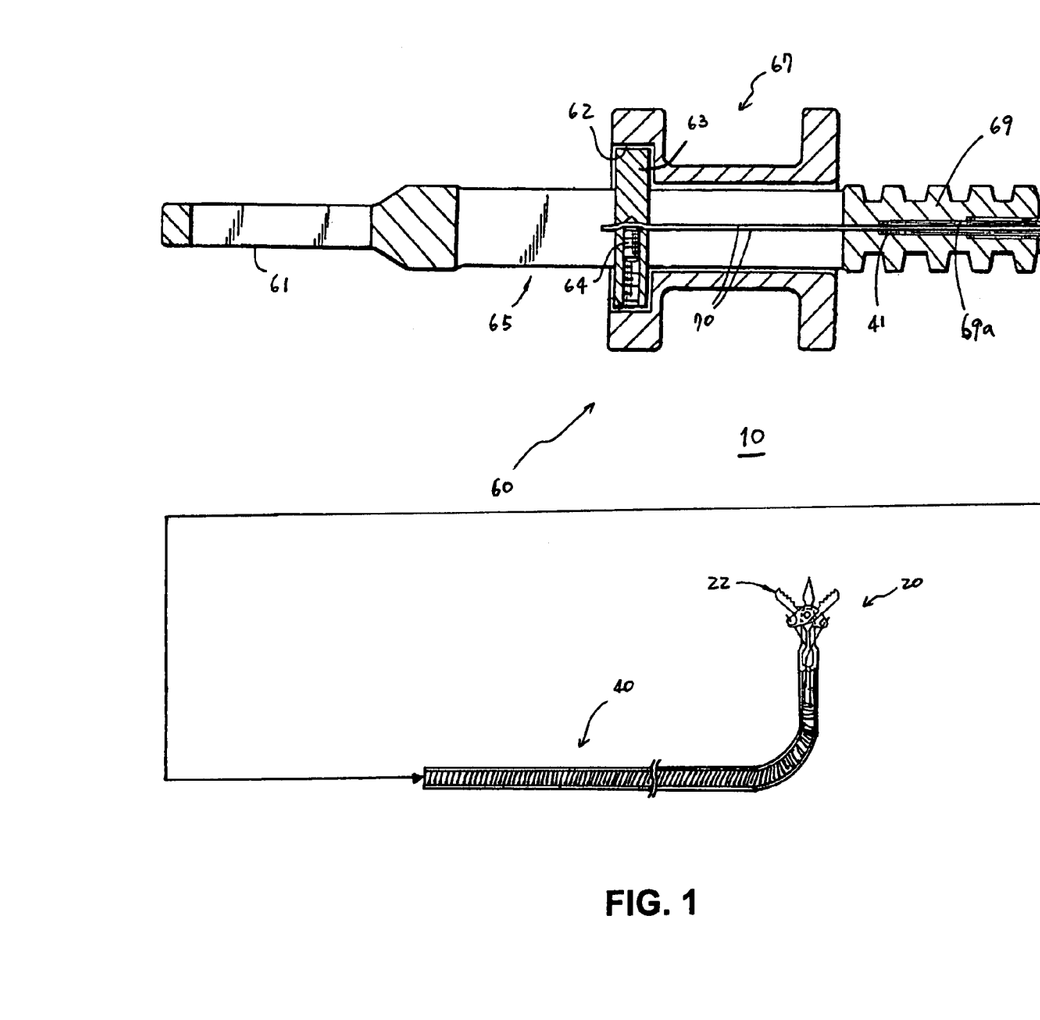
FIG. 1 is a cross-sectional view of a biopsy forceps device having a deflectable distal portion, according to an embodiment of the invention.
Figure 2:
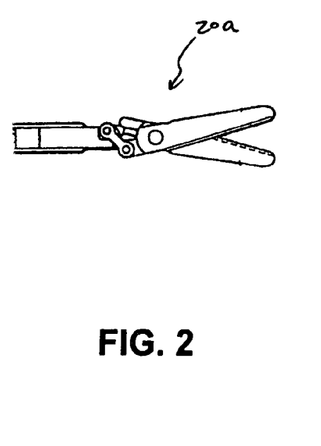
FIG. 2 is a partial cross-sectional view of an alternative end effector assembly (e.g., scissors) for use in a medical device, according to another embodiment of the invention.

According to an exemplary embodiment of the invention, FIG. 1 illustrates a medical device 10 having a capability for deflecting a distal portion of a control shaft so as to facilitate movement of an end effector assembly, such as, for example, biopsy forceps or scissors. While the invention will be described in connection with a particular biopsy forceps device, the invention may be applied to, or used in connection with, any other types of biopsy forceps, numerous other tissue cutting end effector assembly devices, such as, for example, snares, knives, needles, jaws, or scissors 20a (as shown in FIG. 2), or other suitable medical devices that may be used in combination with the control shaft of the invention. The suitable medical devices include, but are not limited to: endoscopic medical devices, such as, for example, needles, fluid injectors, graspers, pincers, or staplers; stent placement/removal devices; dilatation balloons and related mechanical expander devices; sphincterotome devices used in, for example, Endoscopic Retrograde Cholangio Pancreatography (ERCP); tissue or stone retrieval devices, such as, for example, forceps, cytology brushes, baskets, snares, needle biopsies, loop-retrievers, or endoscopic mucosal resection (EMR) devices; hemostasis devices, such as, for example, hemoclip and electrocoagulation probes, or sclerotherapy needles; injection devices used in, for example, chemotherapy, cooling, heating, embolics (solid, liquid; n-Butyl cyanoacrylates (n-BCA or super glue), and crosslinking; Enteryx or Onyx EVOH (ethylene vinyl alcohol), alginate, chitosan and carageenan), dyes, or markers; vacuum devices for fluid removal, tissue lifting, and tissue removal; implantation devices for radiopaque markers or radiation therapy; imaging devices, such as, for example, ultrasound catheters or fiber optics used for visualization or directing light and laser; measurement devices for pH, moisture/dryness, temperature, pressure, or size; dilatation-ureteral balloon or stent catheters; nephrostomy balloon catheters, melecot, dilators, or drainage devices; or lithotripsy devices.

As shown in FIG. 1, the medical device 10 may include an end effector assembly 20, such as biopsy forceps, an elongated control shaft 40, and a proximal handle assembly 60. The device 10 may also include one or more flexible control members 70 extending between the end effector assembly 20 and the handle assembly 60 through a lumen of the control shaft 40.

Figure 3:
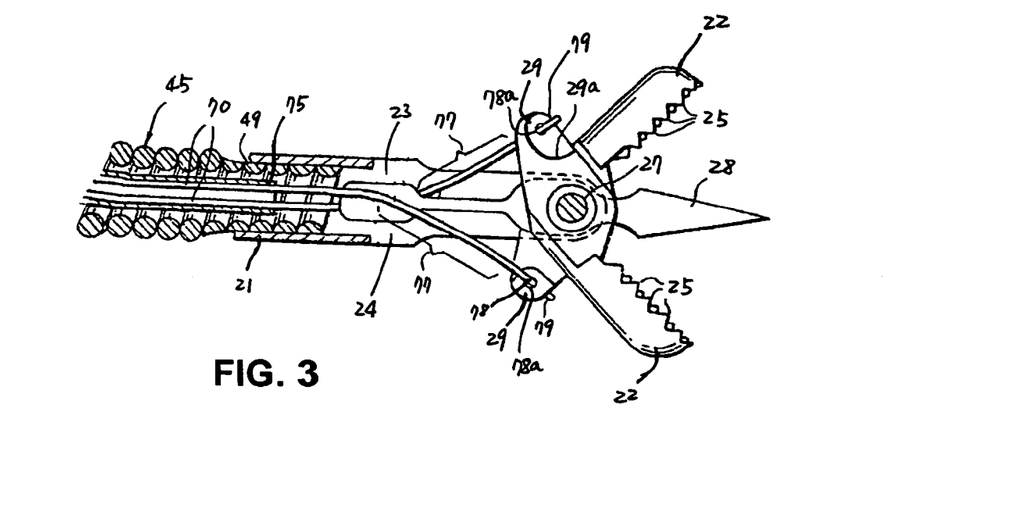
FIG. 3 is an exploded cross-sectional view of the end effector assembly shown in FIG. 1, with its jaws open.
Figure 4:
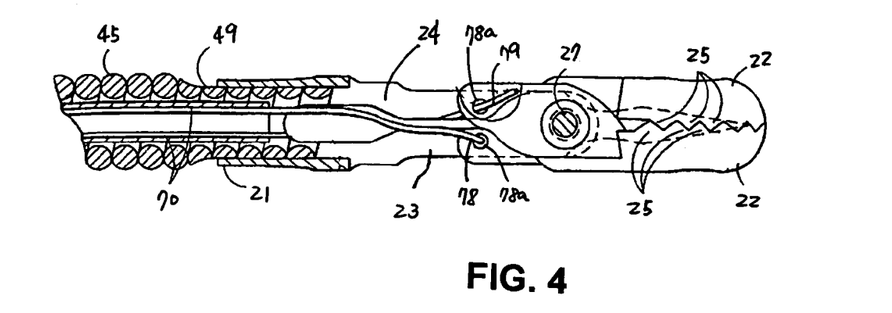
FIG. 4 is an exploded cross-sectional view of the end effector assembly shown in FIG. 1, with its jaws closed.

As best shown in FIGS. 3 and 4, the end effector assembly 20 may include a clevis member 24 to which a pair of jaws 22 may be connected. The clevis member 24 may include a tubular proximal portion 21 and a pair of side arms 23 extending from the tubular proximal portion 21. The clevis member 24 may also include a clevis pin 27, extending from each of the side arms 23 of the clevis member 24. In an exemplary embodiment, the proximal portion 21, the pair of side arms 23, and the clevis pin 27 may be integrally made from a common casting to form the clevis member 24.

Each of the jaws 22 in the end effector assembly 20 may be a duplicate of the other and may include one or more teeth 25 at its distal end portion, preferably aligned radially with respect to a particular reference point. At a predetermined location between the distal and proximal ends of each jaw 22, there is a suitable mechanism for rotatably coupling the jaws 22 with the clevis pin 27 to actuate the movement of the jaws 22 between open and closed positions. In an exemplary embodiment, a bore extending transversely through each jaw 22 may be formed at a midpoint between the distal and proximal ends of each jaw 22 through which the device pin 27 may extend. In this embodiment, the jaws 22 may be rotatably aligned with respect to the clevis pin 27 extended through the bore on each respective jaw 22. The bore may include a suitable bearing member, such as, for example, an annular boss, to reduce friction resulting from the rotational movement of the jaws 22. At its proximal end portion, each jaw 22 may include a tang 29, preferably having a recess 29a on its outer side thereof, for connection with the respective control member 70.

The distal end of the biopsy end effector assembly 20 may include a needle 28 disposed between the two jaws 22. The needle 28 may have a pointed end which may be retracted inside the jaws 22 when the jaws 22 are closed, and a tail which may extend to the distal end portion of the control members 70. The needle 28 may have a central opening through which the clevis pin 27 may extend, as shown in FIGS. 3 and 4.

The elongated control shaft 40 may be sufficiently flexible to traverse through a tortuous body cavity, yet stiff enough to prevent lumen collapse when tension on the control member 70 is generated. For that purpose, the elongated control shaft 40, as shown in FIGS. 3 and 4, may be formed of a wire coil 45. The wire coil 45 may include a coating of suitable biocompatible material, such as, for example, PTFE, PP, PE, Nylon, Pebax, Polyimide, or any other materials known in the art, on the outer surface of the wire coil 45. If the wire coil 45 is used in an electro-active device, the coating may also act as an insulator. Alternatively, or in addition, the control shaft 40 may include a tubular sleeve member, made of a plastic material, such as, for example, Teflon, PTFE, or any other suitable material known in the art. The wire coil 45 may also include a radiopague filler, such as, for example, barium sulfate or tantalum, to enhance visualization under fluoroscopy. In addition, the wire coil 45 may include a hydrophilic lubricious material or other suitable lubricating material to reduce friction. The dimensions of the control shaft 40 may vary depending upon the type of the end effector assembly being used and/or the type of procedure being performed. In an exemplary embodiment, the wire coil 45 may have inner and outer diameters of approximately 0.032 inch (=0.81 mm) and 0.080 inch (=2.0 mm), respectively, and a length of approximately 240 cm.

The distal end portion 49 of the control shaft 40, as best shown in FIGS. 3 and 4, may be flattened for ease of connection between the proximal portion 21 of the clevis member 24 and the distal end of the control shaft 40. In various exemplary embodiments, the distal end of the shaft 40 may be connected to the clevis member 24, with or without the flattened distal end portion 49, via interference-fit, crimping, soldering, welding, fusing, adhesive, or any other suitable connection mechanisms known in the art.

The proximal end 41 of the control shaft 40 may be fixedly secured to the handle assembly 60 via a suitable connection mechanism known in the art. In the exemplary embodiment shown in FIG. 1, the proximal end of the wire coil 45 extends into a bore 69a formed in a distal shaft 69 of the handle assembly 60 and is locked in place by a suitable mechanism. For example, the bore 69a may have a stepped configuration with varying diameter, where a locking coil may be disposed against a larger diameter area and threadedly engage with the wire coil 45 to secure the wire coil 45 to the handle assembly 60.

As also shown in FIG. 1, the device 10 includes a control member 70, such as, for example, a single-filament or multi-filament shaft or wire, used for manipulating the end effector assembly 20 from the handle assembly 60. The control member 70 may be flexible enough to pass through a tortuous body cavity, yet sufficiently stiff to resist minor compressive force, thereby permitting axial movement of the control member 70 relative to the control shaft 40. To aid this purpose, the device 10 may optionally include an inner sleeve 75 (see FIG. 3), such as, for example, FEP sheath, extending from the distal end of the wire coil 45 therethrough into the distal shaft 69 of the handle assembly 60. Alternatively, or in addition, this inner sleeve 75 may act as a bearing member between the control member 70 and the lumen of the control shaft 40. The sleeve 75 may be formed of a plastic material, such as, for example, PTFE, Nylon, Pebax, PP, or PE. If the control member 70 is formed of multi-filament shafts or wires, each individual shaft or wire may be covered with the sleeve material.

In an exemplary embodiment, the control member 70 may be made of stainless steel, nickel-titanium alloy, or a combination of the two, but any other suitable material known in the art may also be used. In another exemplary embodiment, at least a portion of the control member 70 or sleeve 75 may be coated 69, in order to limit twist and movement of the wire coil 45 with the bore of the distal shaft 69 while preventing a sharp bend of the wire coil 45 at the distal end of the handle assembly 60.

As will be described herein, the proximal end of the control member 70, such as, for example, one or more pull wires, may extend through the control shaft 40 and the distal shaft 69, and fixedly secure to the movable spool 67 via a suitable connecting means, such as, for example, a crimp ring or a cross pin. In the embodiment shown in FIG. 1, the end of a cross pin 63 mates with a slot 62 in the spool 67 so as to lock the cross pin 63 therewith. The proximal ends of the pull wires 70 may then be locked into the cross pin 63 by a set screw 64, so that movement of the spool 67 may thereby effectuate movement of the pull wires 70, the distal ends of which are connected to the end effector assembly 20, as shown in FIGS. 3 and 4.

In an application where mono-polar electric current needs to be supplied to the end effector assembly 20, the handle assembly 60 may include a suitable current supplier, such as an active cord connector, that may contact the control member 70. The control member 70 may then act as an electrical conductor to supply the current received from the current supplier to the end effector assembly 20. In an embodiment, the set screw 64 may be replaced by a suitable active cord connector that may contact the control member 70 and supply the electrical current therethrough to the end effector assembly 20.

In an application that may require bi-polar current, the two control members 70 may be insulated from each other, and the handle assembly 60 may with a lubricating material, such as, for example, liquid silicon, to facilitate the axial movement of the control member 70.

As shown in FIGS. 3 and 4, the distal end of each control member 70 may connect to the tang 29 of each jaw 22. The distalmost end of the control members 70 may include a first bent portion 78 which may extend through a bore 78*a* in the tang 29 and a second bent portion 79 which may be rotatably disposed in the recess 29*a* of the tang 29. The first bent portion 78 may form an approximately 90° bend with respect to the main portion of the control member 70. The control member 70 may have a reflex curve 77, to aid opening of the jaws 22 when the spool 67 is moved distally.

As shown in FIG. 1, the handle assembly 60 may include a thumb ring 61 fixedly attached to a main body 65, and a spool 67 slidably coupled to the main body 65, for manipulation of the end effector assembly 20. The spool 67 may be reciprocally slidable along the main body 65 so as to move the control member 70 coupled to the spool 67 relative to the control shaft 40. The spool 67 may be configured to rotate with respect to the axis of the main body 65 so as to control the orientation of the end effector assembly 20. As will be described herein, the reciprocal movement of the spool 67 may control the operation of the end effector assembly 20 as well as the deflection of the distal portion of the control shaft 40.

The handle assembly 60 may include the distal shaft 69, to which the proximal end of the control shaft 40 may be secured via a suitable locking member. Optionally, the distal shaft 69 may include a strain relief sheath (not shown) over the wire coil 45, which may extend slightly distally from the distal end of the distal shaft include two separate active cord connectors each contacting the respective one of the two control members 70, so that supplied bi-polar current may be applied across the jaws 22 of the end effector assembly 20. As mentioned above, the distal end of each control member 70 may be connected to the tang 29 of each jaw 22 of the end effector assembly 20. Each jaw 22 may then be insulated from each other and the clevis pin 27 by a non-conductive material, so that the applied current may flow only when the jaws 22 are in contact with each other or through a mutually conducting medium.

Figure 6:
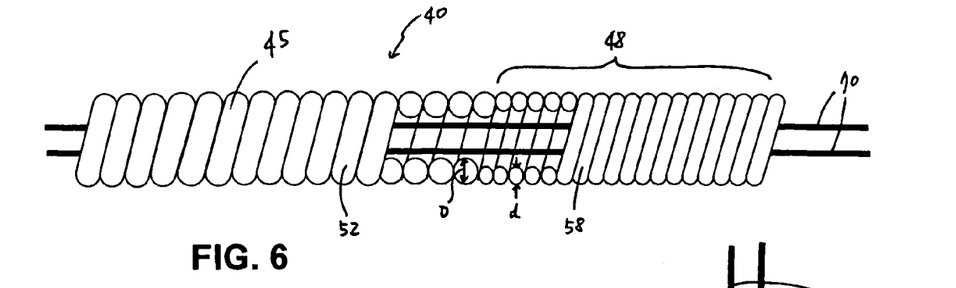
FIG. 6 is a partial schematic view of the control shaft shown in FIG. 1, illustrating a normal, straightened position, according to an embodiment of the invention.
Figure 7:
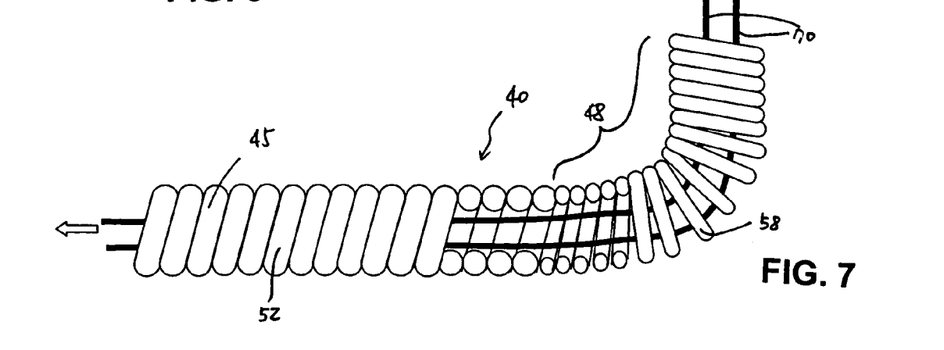
FIG. 7 is a partial schematic view of the control shaft shown in FIG. 1, illustrating a deflected position, according to an embodiment of the invention.

With reference to FIGS. 6 and 7, a control mechanism that may enable deflection of a distal portion 48 of the control shaft 40 so as to facilitate movement of the end effector assembly 20 will be described, according to an exemplary embodiment of the invention. As shown in FIGS. 6 and 7, the distal portion 48 of the control shaft 40 may be configured to exhibit higher flexibility than that of the remaining portion of the control shaft 40. For example, the exemplary control shaft 40 shown in FIGS. 6 and 7 may be formed of a wire coil 45, and the distal portion 48 of the wire coil 45 is formed by a wire 58 having a diameter, d, that is smaller than a diameter, D, of a wire 52 in the remaining portion of the wire coil 45. The inner diameter of the wire coil 45 may remain substantially the same throughout the length of the wire coil 45. In an exemplary embodiment, for example, the distal portion 48 of the wire coil 45 may have an outer diameter of approximately 0.072 inch (=1.83 mm), an inner diameter of approximately 0.032 inch (=0.81 mm), and a wire diameter of approximately 0.020 inch (=0.51 mm), while the remaining portion of the wire coil 45 may have an outer diameter of approximately 0.080 inch (=2.0 mm), an inner diameter of approximately 0.032 inch (=0.81 mm), and a wire diameter of approximately 0.024 inch (=0.70 mm). It is to be understood that varying the flexibility of the control shaft 40 may be applied to any portion of the control shaft 40, including the distal portion 48, as shown in this example.

Figure 15:
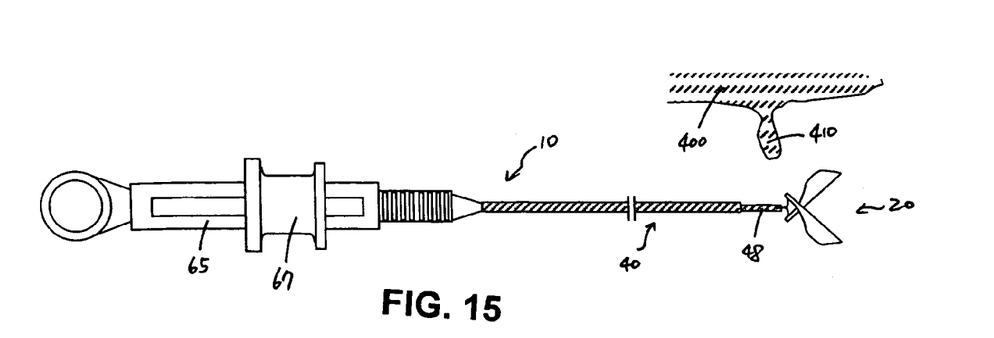
Figure 16:
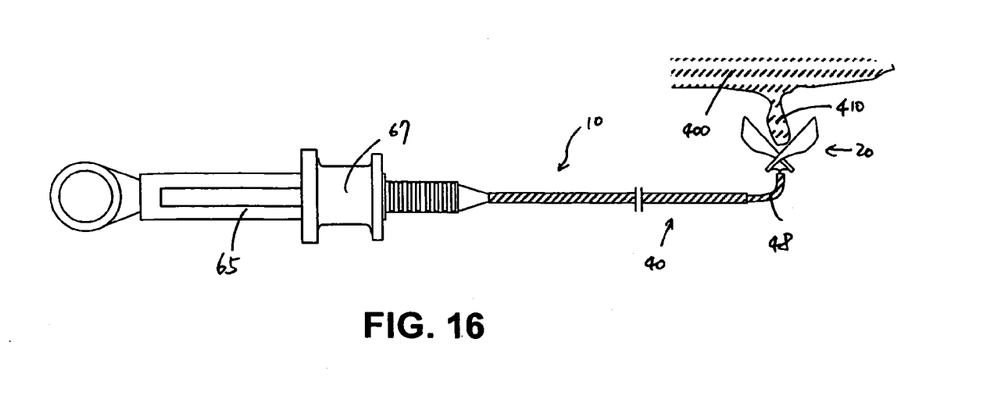

As will be described in more detail herein, this enhanced flexibility in the distal portion 48 relative to the remaining portion of the control shaft 40 allows selective deflection of the distal portion 48, thereby enhancing the movement of the end effector assembly 20, as shown in FIG. 7. For example, the spool 67 of the handle assembly 60 may be advanced distally to fully open the end effector assembly 20, as shown in FIG. 15 and to be described in more detail further herein. Upon further advancement of the spool 67 in the distal direction, additional pressure may be exerted on the control member 70, and the distal portion 48 having the higher flexibility than the remaining portion of the control shaft 40 may begin to deflect, as shown in FIGS. 7 and 16. Depending on the desired degree of deflection, a physician operating the device 10 may readily control the deflection by appropriately adjusting the movement of the spool 67.

Alternatively or additionally, in accordance with another embodiment of the invention, the flexibility may be adjusted by utilizing a wire material that has different characteristics from the material characteristics of the wire in the remaining portion. These material characteristics include, but are not limited to, tensile strength, shear strength, or ductility, so as to adjust the desired flexibility of the distal portion 48, with or without altering the wire diameter in the distal portion 48 of the control shaft 40.

Figure 8:
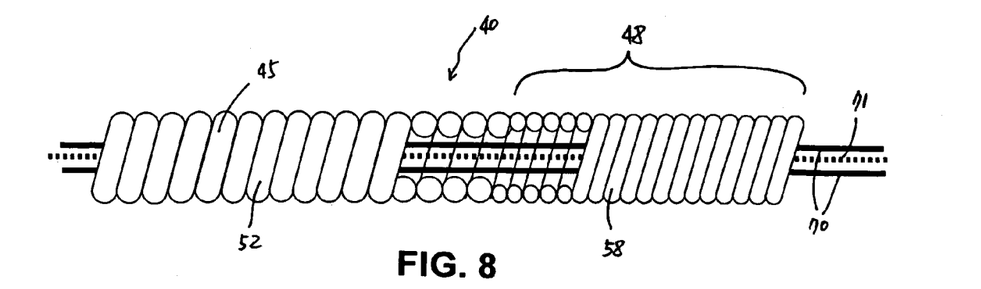
FIG. 8 is a partial schematic view of the control shaft shown in FIG. 1, illustrating a deflection control member, according to another embodiment of the invention.
Figure 10A:
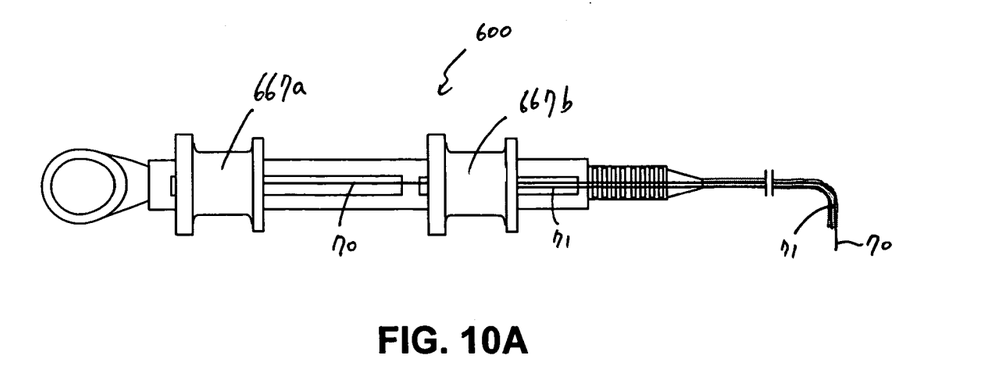
FIGS. 10A–C are schematic views of various handle assemblies, illustrating various arrangements for a controller of a deflection control member, according to various embodiments of the invention.
Figure 10B:
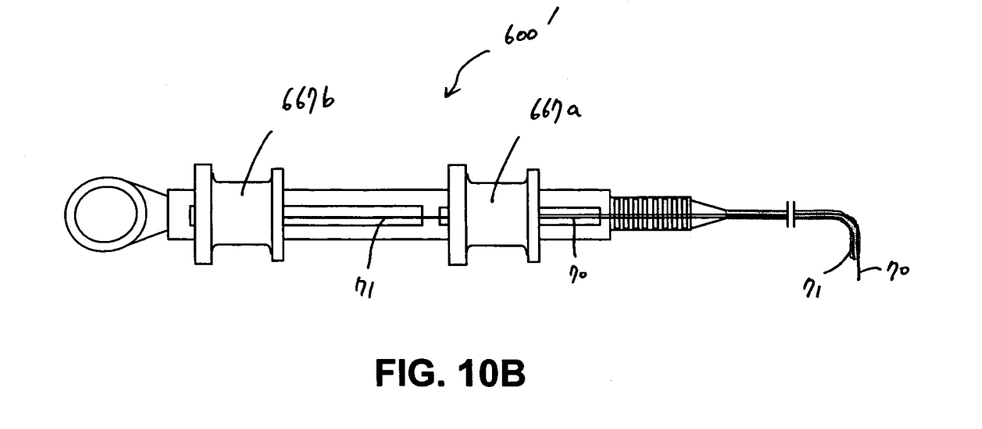
Figure 10C:
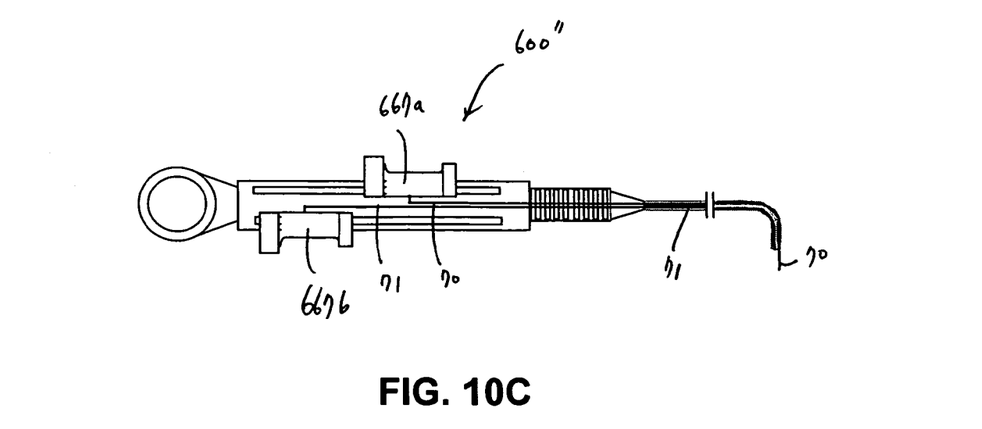

In still another exemplary embodiment of the invention, the wire coil 45 may be provided with a deflection control member 71, such as, for example, a flexible shaft or wire, controlling the deflection of the distal portion 48, together with the control member 70, as shown in FIG. 8. In this exemplary embodiment, the handle assembly 60 may integrally or separately include a suitable deflection controller for the deflection control member 71. For example, as shown in FIGS. 1A, a deflection controller for the deflection control member 71 may be provided as an additional spool 667*b* integrally formed in a handle assembly 600 together with the spool 667*a* for controlling the operation of the end effector assembly. By this arrangement, the deflection of the control shaft may be independently operated by the additional spool 667*b*. While FIG. 10A shows the additional spool 667*b* disposed distal to the spool 667*a*, it may also be positioned proximal to the spool 667*a*, as shown in FIG. 10B. Alternatively, the spools 667*a* and 667*b* may be configured and positioned along the main body of the handle assembly 600″, as shown in FIG. 10C, so that the spools may slide past one another. The spools shown in the FIG. 10C embodiment are of a hemispheric shape to permit translation past one another. The handle assemblies 600, 600', 600″ shown in FIGS. 10A–10C may include suitable locking and/or stopping mechanisms, such as, for example, a locking slot, a stopper, or any other mechanism known in the art.

In operation, once the distal portion 48 is deflected, the deflection control member 71 may be used to hold the distal portion 48 in the deflected position by actuating or locking the deflection controller 667*b*. Alternatively, the deflection control member 71 may independently control the deflection of the distal portion 48 by a suitable, separately arranged deflection controller. The deflection control member 71 may then be actuated, independent from the control member 70, so as to deflect, hold, and/or straighten the distal portion 48 of the control shaft 40. For this purpose, a distal end of the deflection control member 71 may be connected to a portion of the distal portion 48. Other operational aspects of these exemplary embodiments may be similar to the exemplary embodiment described with reference to FIGS. 14–18.

Figure 9:
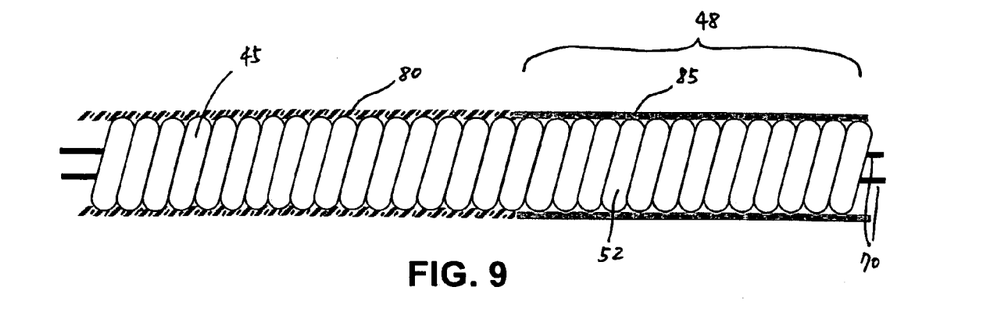
FIG. 9 is a partial schematic view of the control shaft shown in FIG. 1, illustrating jacketing of the control shaft, according to still another embodiment of the invention.

In still another exemplary embodiment of the invention, the wire coil 45 may be provided with a jacket 80 covering at least a portion of the outer surface of the wire coil 45 in the region other than the distal portion 48 intended to be deflected, as shown in FIG. 9. The jacket may create an additional stiffness in the covered region, rendering the uncovered distal portion 48 relatively more flexible than the covered proximal region. Jacketing the wire coil 45 may also allow the deflection of the distal portion 48 without modifying the coil in the distal portion 48. In an exemplary embodiment, the jacket may be made of a polymer material, such as, for example, PTFE, PP, PE, Nylon, Pebax, Polyimide, or any other suitable material.

In another exemplary embodiment, the distal portion 48 of the wire coil 45 may also be provided with another jacket 85 with a material softer than the material of the jacket 80 in the proximal region, as shown in FIG. 9. For example, the distal portion 48 may be provided with the jacket 85 made of, for example, Pebax 2533, while the remaining portion of the wire coil 45 may be provided with the jacket 80 made of, for example, Nylon 12, as shown in FIG. 9.

Figure 5:
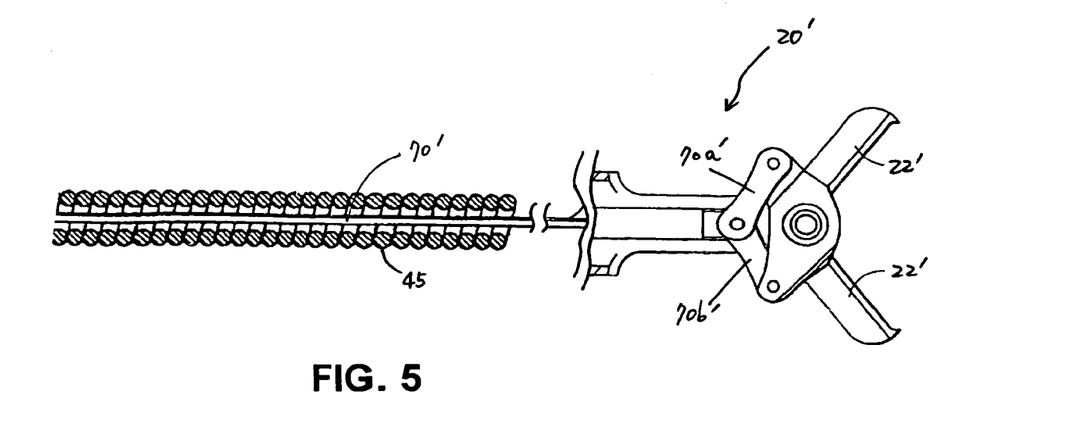
FIG. 5 is an exploded cross-sectional view of another end effector assembly for use in a medical device, according to an embodiment of the invention.

The handle assemblies 60, 600, 600', 600″ shown and described in FIGS. 1, 10A–C, 11, and 14–18 are exemplary only. Other handles known in the art that can actuate an end effector assembly may be used. For example, a handle assembly may include a scissors-like actuation mechanism or different actuation mechanism for operating the end effector assembly 20. In addition, while the invention is described in connection with a particular double-acting biopsy jaw assembly, the handle assemblies 60, 600, 600', 600″ shown in FIGS. 1, 10A–C, 11, and 14–18 or any other suitable handle assemblies may be used to actuate a single-acting end effector assembly 20' shown in FIG. 5, which requires only a single control member 70' for operation of jaws 22'. In the embodiment shown in FIG. 5, the control member 70' couples to links 70*a'*, 70*b'* that connect to the respective jaws 22' to open and close the jaws 22'.

In operation, as shown in FIGS. 3 and 4, the end effector assembly 20 may be opened by extending the control member 70 distally and closed by retracting the control member 70 proximally. Since the control member 70 may be coupled to the spool 67 of the handle assembly 60, the opening and closing operations of the end effector assembly 20 may be controlled by reciprocating the spool 67 relative to the main body 65 and the control shaft 40.

Figure 11:
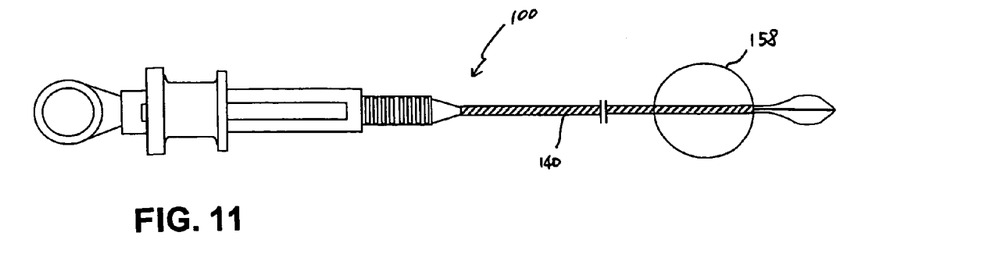
FIGS. 11–13 are schematics for illustrating an exemplary method of making the device of FIG. 1, according to an embodiment of the invention.
Figure 12A:
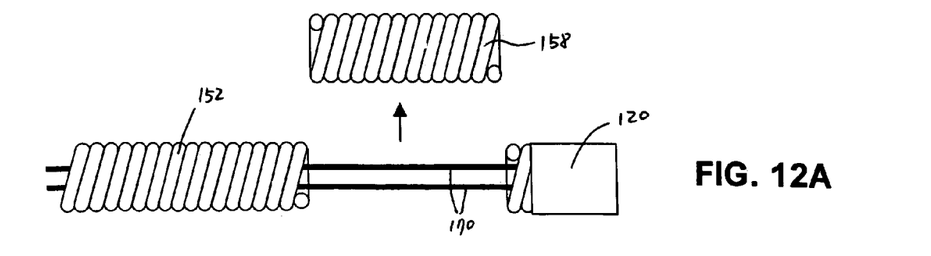

FIGS. 11, 12A, 12B, and 13 show a method of making an exemplary device 10 of the invention from an existing medical device 100 shown in FIG. 11, according to another embodiment of the invention. As shown in FIG. 12A, a distal portion 158 of a control shaft 140 may be cut and removed from the existing medical device 100. The length of the distal portion 158 to be cut may vary depending on the type of the medical procedures the device is intended to perform. In an exemplary embodiment, it may range from about 0.5 inch to about 3 inch, and more preferably about 1.0 inch.

Figure 12B:
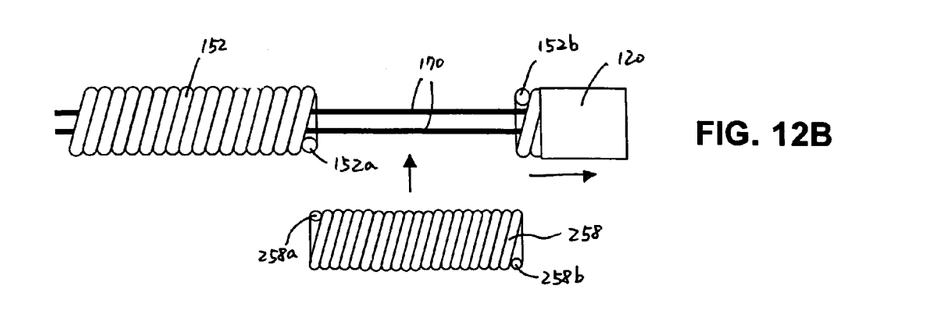
Figure 13:
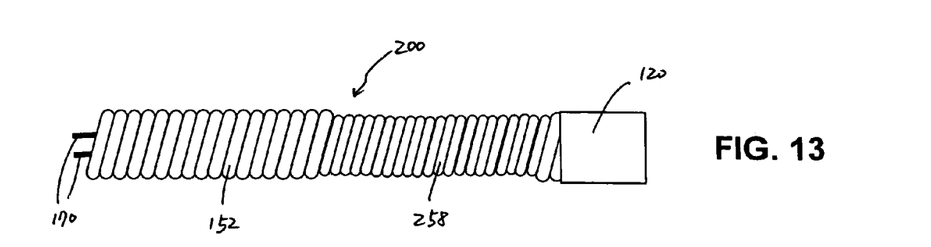

For the cutting and removing steps, the control shaft 140 may be separated from the device 100 by temporarily removing the end effector assembly 120 (represented simply as a box in FIGS. 12A, 12B, and 13) or the proximal handle assembly (not shown) in order not to interfere with the control members 170. Once the distal portion 158 is removed, a replacement coil section 258 having a wire diameter smaller than a diameter of the existing wire 152 may be placed in the removed section, as shown in FIG. 12B. The ends 258*a*, 258*b* of the replacement section of wire coil 258 may be, for example, laser-welded to the ends 152*a*, 152*b* of the existing wire coil 152. Other alternative interconnecting mechanisms, such as, for example, soldering, arc welding, brazing, or crimping may be used to connect the replacement coil section 258 to the existing device 100. Should the axial movement of the spool 67 be limited due to configuration of the handle assembly and an adjustment in the length of the control member 70 is not desired, in accordance with another exemplary embodiment, the replacement coil section 258 may have a length less than the length of the removed distal portion 158 in order to enable the existing handle assembly to fully control the deflection of the replacement coil section 258. A deflection control member (not shown), similar to the deflection control member 71 shown in FIG. 8, may be used to independently, or in cooperation with the control member 170, deflect, hold, and/or straighten the distal portion 158 or the replacement coil section 258 of the control shaft 140. The distal portion of the modified device 200, according to an embodiment of the invention, is shown in FIG. 13.

Alternatively, instead of replacing the distal portion of a control shaft from an existing medical device, a central shaft for a medical device may initially be made with a length smaller than the total desired shaft length, so that a length of more flexible coil may be added to the control shaft. The complete shaft may be connected to a handle and end effector assembly.

According to still another embodiment, a control shaft may be made of a unitary coil. Various manufacturing processes may then be used to provide a greater flexibility to the distal portion relative to the remaining portion of the shaft. For example, the distal portion of the shaft may have a coil-wound density less than that of the remaining portion, so as to have a relatively greater flexibility in the distal portion. Alternatively, or in addition, the distal portion or the remaining portion of the shaft may be selectively subjected to a material processing, such as, for example, a cold working or annealing process, that may alter the material flexibility, so as to render the distal portion relatively more flexible than the remaining portion.

The operation of the device 10, according to an embodiment of the invention, will be described in detail with reference to FIGS. 3, 4, and 14–18. While operational aspects of the invention will be described with an exemplary embodiment shown in FIGS. 6 and 7, and in connection with a particular tissue cutting procedure, the invention may be applied to other suitable medical procedures, or used in connection with any other suitable end effector assemblies, without departing from the scope of the invention. For example, instead of cutting tissue, the invention may be applied to other various medical devices, such as, for example, imaging devices, tissue or stone retrieval devices, injection devices, grasping devices, suturing devices, stapling devices, stent placement/removal devices, dilatation devices, sphincterotome devices, hemostasis devices, vacuum devices, marker implantation devices, measurement devices, ureteral devices, nephrostomy balloon devices, lithotripsy devices, and the suitable medical procedures associated with such devices.

Figure 14:
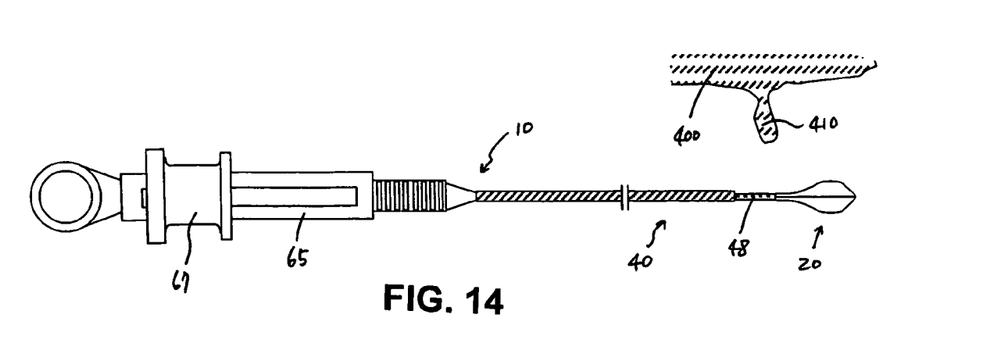
FIGS. 14–18 are schematics illustrating an exemplary method of a surgical procedure using the device of FIG. 1, according to an embodiment of the invention.

FIG. 4 illustrates a closed position of the end effector assembly 20. To attain this position, the spool 67 may be moved proximally relative to the main body 65 to retract the control member 70 proximally, causing the end effector assembly 20 to close. This closed position of the end effector assembly 20 may be the preferred position while inserting the device 10 into a body cavity. With this position of the end effector assembly 20, the device 10 may be inserted into an endoscope lumen to position the distal end of the device 10 near the tissue site 400, as shown in FIG. 14. A suitable imaging device, such as, for example, an endoscope, colonoscope, or sigmoidoscope, may be used to aid in positioning the distal end of the device 10.

Once the distal end of the device 10 is properly positioned, the spool 67 may be moved distally relative to the main body 65 to push the control member 70 distally, causing the end effector assembly 20 to open, as shown in FIGS. 3 and 15. From this position, depending on the location and orientation of target tissue 410 to be severed, the distal portion of the device 10 may be manipulated appropriately, including deflection of the distal portion 48, to receive tissue in the end effector assembly 20. It should be understood that the deflection step may occur prior to opening the end effector assembly 20.

In an exemplary embodiment, for example, to deflect the distal portion 48 of the wire coil 45, the spool 67 of the handle assembly 60 may be further advanced distally, as shown in FIG. 16, exerting more pressure on the control member 70 and, thereby, causing the distal portion 48 to deflect. Depending on the desired degree of deflection, a physician operating the device 10 may readily control the deflection by appropriately adjusting the movement of the spool 67. This enhanced deflection capability of the distal portion 48 may sufficiently enable the physician to accurately receive the target tissue 410 inside the jaws of the end effector assembly 20, as shown in FIG. 16.

Figure 17:
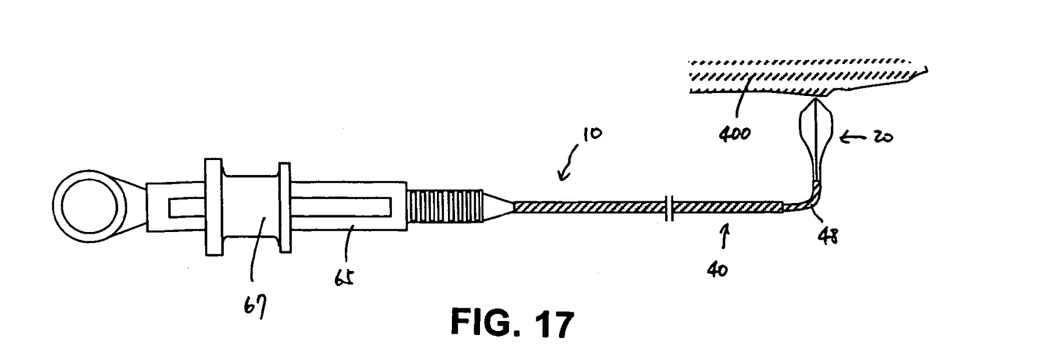
Figure 18:
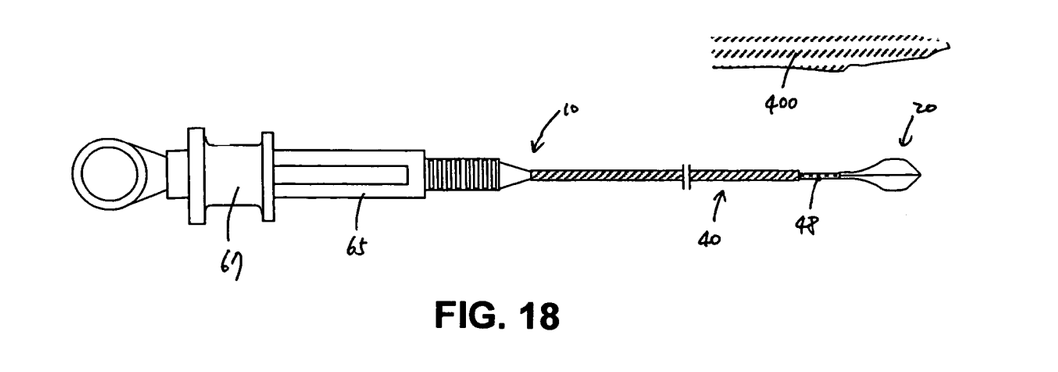

Once the target tissue 40 is received in the end effector assembly 20, the contact between the end effector assembly 20 and the target tissue 410 may sufficiently prevent the control shaft 40 from straightening prior to closing the jaws. The spool 67 may then be moved proximally relative to the main body 65 to move the control member 70 proximally, causing the end effector assembly 20 to close and sever the target tissue received in the end effector assembly 20, as shown in FIG. 17. Optionally or in alternative, a deflection control member (not shown) may be used to hold the distal portion 48 of the wire coil 45 in the deflected position until the target tissue is severed. In an embodiment, an independent deflection controller may be used to control the deflection of the distal portion 48, independent from the operation of the end effector assembly 20. After the target tissue is removed, the physician may release the tension in the control member 70 by slowing allowing the spool 67 to come to rest, causing the distal portion to return to its normal, straightened position, as shown in FIG. 18. The physician may then, if desired, repeat any portion of the medical procedure described above, in any order, or remove the device from the patient's body.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device for use with an endoscope, comprising:
a proximal handle;
a distal assembly for performing a medical procedure; and
an elongated member connecting the proximal handle to the distal assembly, the elongated member having a proximal portion and a distal portion, the distal portion having a flexibility greater than a flexibility of the proximal portion so as to selectively deflect the distal portion relative to the proximal portion,
wherein actuation of a single moving part of the proximal handle causes both deflection of the distal portion and actuation of the distal assembly to perform the medical procedure.

2. The device of claim 1, wherein the elongated member includes a wire coil.

3. The device of claim 2, wherein the wire coil at the distal portion has an outer diameter that is less than an outer diameter of the wire coil at the proximal portion.

4. The device of claim 2, wherein the distal portion is made of a first wire and the proximal portion is made of a second wire, the first wire having a diameter less than a diameter of the second wire.

5. The device of claim 1, further comprising a jacket covering an outer surface of the proximal portion of the elongated member.

6. The device of claim 1, wherein the proximal portion includes a first outer jacket and the distal portion includes a second outer jacket, wherein the second outer jacket is made of a material different than a material of the first outer jacket, so that the distal portion is more flexible than the proximal portion.

7. The device of claim 6, wherein the second outer jacket material is softer than the first outer jacket material.

8. The device of claim 6, wherein the elongated member includes a wire coil made of a wire having substantially the same diameter.

9. The device of claim 1, wherein the movable part is configured to actuate from a first position to a second position to actuate the distal assembly and from the second position to a third position to deflect the distal portion relative to the proximal portion.

10. The device of claim 9, wherein the movable part moves relative to a stationary part of the handle between the first, second, and third positions.

11. The device of claim 10, wherein the movable part is axially reciprocally movable relative to the stationary part.

12. The device of claim 1, further comprising a deflection control member configured to hold the distal portion in a deflected position.

13. The device of claim 1, further comprising a deflection control member for controlling the deflection of the distal portion relative to the proximal portion.

14. The device of claim 1, wherein the distal assembly includes a biopsy forceps assembly.

15. A medical device for use with an endoscope, comprising:
a proximal handle;
a distal assembly for performing a medical procedure;
an elongated member connecting the proximal handle to the distal assembly, actuation of the proximal handle causing the distal assembly to perform the medical procedure, the elongated member having a distal portion and a proximal portion; and
a deflection control member passing through the elongated member and having a proximal end connected to the proximal handle and a distal end connected to the distal portion of the elongated member,
wherein moving the deflection control member proximally relative to the elongated member causes the distal portion to deflect relative to the proximal portion.

16. The device of claim 15, further comprising:
a first outer jacket covering at least a portion of the proximal portion of the elongated member; and
a second outer jacket covering at least a portion of the distal portion of the elongated member,
wherein the second outer jacket includes a material that is softer than a material of the first outer jacket.

17. The device of claim 15, wherein the elongated member includes a wire coil.

18. The device of claim 16, wherein the distal portion is made of a first wire and the proximal portion is made of a second wire, the first wire having a diameter less than a diameter of the second wire.

19. The device of claim 15, wherein the elongated member includes a wire coil made of a wire having substantially the same diameter.

20. The device of claim 15, wherein actuation of the handle causes at least one of actuation of the distal assembly and deflection of the distal portion.

21. The device of claim 20, wherein actuation of handle from a first position to a second position actuates the distal assembly, and actuation of handle from the second position to a third position deflects the distal portion relative to the proximal portion.

22. The device of claim 21, wherein the handle includes a stationary part and a movable part movable relative to the stationary part between the first, second, and third positions.

23. The device of claim 22, wherein the movable part is axially reciprocally movable relative to the stationary part.

24. The device of claim 15, wherein the deflection control member is configured to hold the distal portion in a deflected position.

25. The device of claim 15, wherein the handle includes a first actuation member for actuating the distal assembly and a second actuation member for deflecting the distal portion.

26. The device of claim 15, wherein the distal assembly includes a biopsy forceps assembly.

27. An elongated control shaft for use in a medical device, comprising:
a wire coil having a proximal portion comprised of a first wire and a distal portion comprised of a second wire, the wire coil configured to connect a handle to a distal assembly, and
a deflection control member configured to connect between the distal portion and the handle such that actuation of the handle causes the distal portion to selectively deflect relative to the proximal portion,
wherein the second wire has a wire diameter less than a wire diameter of the first wire, so that the distal portion of the wire coil has a flexibility greater than a flexibility of the proximal portion.

28. The shaft of claim 27, wherein the wire coil at the distal portion has an outer diameter that is less than an outer diameter of the wire coil at the proximal portion.

29. The shaft of claim 27, further comprising a jacket covering at least a portion of an outer surface of the wire coil.

30. The shaft of claim 27, wherein the deflection control member is configured to hold the distal portion in a deflected position.

31. An elongated control shaft for use in a medical device, comprising:
an elongated member for connecting a proximal handle to a distal assembly, wherein actuation of the proximal handle causes the distal assembly to perform a medical procedure, the elongated member having a proximal portion and a distal portion; and
a deflection control member passing through the elongated member and having a proximal end for connecting to the proximal handle and a distal end connected to the distal portion of the elongated member,
wherein the elongated member and the deflection control member are configured such that moving the deflection control member proximally relative to the elongated member causes the distal portion to deflect relative to the proximal portion.

32. The shaft of claim 31, further comprising:
a first outer jacket covering at least a portion of the proximal portion of the elongated member; and
a second outer jacket covering at least a portion of the distal portion of the elongated member,
wherein the second outer jacket includes a material that is softer than a material of the first outer jacket.

33. The shaft of claim 31, wherein the elongated member includes a wire coil.

34. The shaft of claim 33, wherein the distal portion is made of a first wire and the proximal portion is made of a second wire, the first wire having a diameter less than a diameter of the second wire.

35. The shaft of claim 33, wherein the elongated member includes a wire coil made of a wire having substantially the same diameter.

36. The shaft of claim 21, wherein the deflection control member is configured to hold the distal portion in a deflected position.

37. A method of making a medical device, comprising:
providing an elongated member having a distal portion and a proximal portion;
attaching a proximal handle to the proximal portion;
extending a deflection control member through the elongated member;
connecting a proximal end of the deflection control member to the proximal handle;
connecting a distal end of the deflection control member to the distal portion of the elongated member, wherein the elongated member and the deflection control member are configured such that moving the deflection control member proximally relative to the elongated member causes the distal portion to deflect relative to the proximal portion; and
attaching a distal assembly for performing a medical procedure to the distal portion.

38. The method of claim 37, further comprising:
jacketing at least a portion of the proximal portion with a first outer jacket; and
jacketing at least a portion of the distal portion with a second outer jacket, wherein the second outer jacket is made of a material softer than a material for the first outer jacket.

39. The method of claim 37, further comprising forming the elongated member with a wire coil.

40. The method of claim 39, wherein forming the elongated member includes forming the distal portion with a first wire and the proximal portion with a second wire, the first wire having a diameter less than a diameter of the second wire.

41. The method of claim 40, wherein the first wire and the second wire are formed from the same wire.

42. The method of claim 40, wherein the first wire is attached to the second wire.

43. The method of claim 37, further comprising providing a first controller in the proximal handle for actuating the distal assembly and a second controller in the proximal handle for controlling deflection of the distal portion.

44. The method of claim 37, further comprising attaching a control member extending from the proximal handle to the distal assembly, wherein the control member is configured to control actuation of the distal assembly.

45. A method of performing a medical procedure, the method comprising:
providing a medical device adjacent to a tissue site, the medical device including a proximal handle, a distal assembly, and an elongated member connecting the distal assembly to the proximal handle;
actuating the distal assembly by actuating a single movable part of the handle from a first position to a second position;
deflecting the distal portion relative to the proximal portion to access tissue at the tissue site by actuating the movable part of the handle from the second position to a third position; and
performing the medical procedure on the tissue with the distal assembly.

46. The method of claim 45, wherein the distal portion of the elongated member has a flexibility greater than a flexibility of a proximal portion of the elongated member.

47. The method of claim 45, wherein the elongated member is configured to selectively deflect the distal portion relative to the proximal portion.

48. The method of claim 45, wherein the elongated member includes a wire coil.

49. The method of claim 48, wherein the wire coil includes the proximal portion made of a first wire and a distal portion made of a second wire, the second wire having a diameter less than a diameter of the first wire, so that the distal portion of the wire coil has a flexibility greater than a flexibility of the proximal portion.

50. The method of claim 48, wherein the wire coil at the distal portion has an outer diameter that is less than an outer diameter of the wire coil at the proximal portion.

51. The method of claim 45, wherein actuating the distal assembly includes opening an end effector assembly of the distal assembly.

52. The method of claim 45, wherein the elongated member includes a first outer jacket covering an outer surface of the proximal portion.

53. The method of claim 52, wherein the elongated member further includes a second outer jacket covering an outer surface of the distal portion, the second outer jacket being made of a material different than a material of the first outer jacket, so that the distal portion is more flexible than the proximal portion.

54. The method of claim 53, wherein the second outer jacket material is softer than the first outer jacket material.

55. The method of claim 45, wherein the movable part of the handle moves relative to a stationary part of the handle between the first, second, and third positions.

56. The method of claim 55, wherein the movable part is axially reciprocally movable relative to the stationary part.

57. The method of claim 45, further comprising holding the distal portion in a deflected position.

58. The method of claim 57, wherein holding the distal portion in the deflected position is performed after deflecting the distal portion and while performing the medical procedure on the tissue.

59. The method of claim 57, wherein holding the distal portion in the deflected position is performed by a deflection control member.

60. The method of claim 45, wherein the distal assembly includes a biopsy forceps assembly.

61. The method of claim 60, further comprising:
opening the biopsy forceps assembly;
receiving the tissue in the biopsy forceps assembly by deflecting the distal portion of the elongated member; and
severing the tissue by closing the biopsy forceps assembly.

62. The method of claim 61, wherein actuating the proximal handle includes actuating the biopsy forceps assembly to open and close.

63. The method of claim 45, wherein performing the medical procedure on the tissue includes closing an end effector assembly of the distal assembly.

64. The method of claim 45, wherein providing a medical device adjacent to a tissue site comprises inserting the medical device into an endoscope.

* * * * *

UNITED STATES PATENT AND TRADEMARK OFFICE
CERTIFICATE OF CORRECTION

| | | |
|---|---|---|
| PATENT NO. | : 7,052,489 B2 | Page 1 of 1 |
| APPLICATION NO. | : 10/727626 | |
| DATED | : May 30, 2006 | |
| INVENTOR(S) | : John A. Griego et al. | |

It is certified that error appears in the above-identified patent and that said Letters Patent is hereby corrected as shown below:

Col. 9, line 19, after "be coated," insert text from col. 9, line 49 (after "assembly 60 may") through col. 10, line 13 (before "include two separate").

Signed and Sealed this

Twenty-eighth Day of July, 2009

JOHN DOLL
*Acting Director of the United States Patent and Trademark Office*